United States Patent
Yuan et al.

(10) Patent No.: US 6,353,103 B1
(45) Date of Patent: *Mar. 5, 2002

(54) ISOQUINOLINAMINE AND PHTHALAZINAMINE DERIVATIVES: CORTICOTROPIN-RELEASING FACTOR RECEPTOR $CRF_1$ SPECIFIC LIGANDS

(75) Inventors: Jun Yuan, Guilford; Taeyoung Yoon, East Haven, both of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/648,200
(22) Filed: Aug. 25, 2000

Related U.S. Application Data

(60) Division of application No. 09/102,310, filed on Jun. 22, 1998, now Pat. No. 6,114,530, which is a continuation-in-part of application No. 08/768,987, filed on Dec. 18, 1996, now abandoned.

(51) Int. Cl.[7] .................... C07D 237/26; C07D 217/22; A61K 31/50; A61K 31/47
(52) U.S. Cl. .................... 544/235; 546/143; 514/247; 514/310
(58) Field of Search .................... 344/235; 546/143; 514/247, 310

(56) References Cited

U.S. PATENT DOCUMENTS 6,114,530 A * 9/2000 Yuan

* cited by examiner

Primary Examiner—D. Margaret Seaman
(74) Attorney, Agent, or Firm—McDonnell Boehnen Hulbert & Berghoff

(57) ABSTRACT

Disclosed are compounds that are highly selective partial agonists or antagonists at human $CRF_1$ receptors that are useful in the diagnosis and treatment of treating stress related disorders such as post traumatic stress disorder (PTSD) as well as depression, headache and anxiety. The compounds have the formula

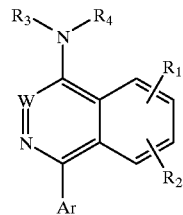

I or the pharmaceutically acceptable salts thereof wherein Ar, $R_1$, $R_2$, $R_3$, $R_4$ and W are various organic and inorganic substituents.

29 Claims, No Drawings

ISOQUINOLINAMINE AND PHTHALAZINAMINE DERIVATIVES: CORTICOTROPIN-RELEASING FACTOR RECEPTOR CRF₁ SPECIFIC LIGANDS

This is a divisional of application Ser. No. 09/102,310, filed Jun. 22, 1998, now U.S. Pat. No. 6,114,530, which is a continuation-in-part of application Ser. No. 08/768,987, filed Dec. 18, 1996 now abandoned.

BACKGROUND OF THE INVENTION

1. Field of the Invention

This invention relates to isoquinolinamine and phthalazinamine derivatives which selectively bind to corticotropin-releasing factor (CRF) receptors. This invention also relates to pharmaceutical compositions comprising such compounds. It further relates to the use of such compounds in treating stress related disorders such as post traumatic stress disorder (PTSD) as well as depression, headache and anxiety.

2. Description of the Related Art

Isoquiolinamines and phthalazinamines have been described in the prior art. For example, Sindler-Kulyk et al, *J. Org. Chem.*, 48(8), 1275–81, (1983) describe a 1-phenyl-4-isoquinolinamine. British Patent GB 1303061 disclose aminophthalazines said to have antiinflammatory activity. Holava et al., *J. Med. Chem.*, 12, 555–6, (1969), describe a 4-phenyl-1-phthalazinamine.

SUMMARY OF THE INVENTION

This invention provides novel compounds of Formula I which interact with CRF receptors.

The invention provides pharmaceutical compositions comprising compounds of Formula I. It further relates to the use of such compounds in treating stress related disorders such as post traumatic stress disorder (PTSD) as will as depression, headache and anxiety. Accordingly, a broad embodiment of the invention is directed to a compound of Formula I:

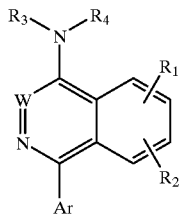

I wherein
Ar is phenyl, 1- or 2-naphthyl, 2-, 3-, or 4pyridinyl, 2- or 3thienyl, 4- or 5pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the phthalazinamine or isoquinolinamine ring is substituted;

$R_1$ and $R_2$ are the same or different and represent
hydrogen, $C_1$–$C_6$ alkyl, halogen, hydroxy, $C_1$–$C_6$ alkoxy,
NH₂, NH($C_1$–$C_6$ alkyl), N($C_1$–$C_6$ alkyl)₂, NO₂, cyano, trifluoromethyl;

$R_3$ and $R_4$ are the same or different and represent
hydrogen, $C_1$–$C_6$ alkyl optionally substituted with halogen, hydroxy, or $C_1$–$C_6$ alkoxy; or aryl($C_1$–$C_6$)alkyl, where aryl is phenyl, 1- or 2-naphthyl, 2-, 3-, or 4-pyridinyl, 2- or 3-thienyl or 2-, 4-, or 5-pyrimidinyl, each of which is optionally mono- or disubstituted with halogen, hydroxy, $C_1$–$C_6$ alkyl, $C_1$–$C_6$ alkoxy; or $C_1$–$C_6$ alkyl-Y—$R_5$, wherein Y is O, S NH, N($C_1$–$C_6$ alkyl), and $R_5$ is hydrogen or $C_1$–$C_6$ alkyl; and W is N or C—$R_6$, where in $R_6$ is hydrogen or $C_1$–$C_6$ alkyl.

These compounds are highly selective partial agonists or antagonists of CRF receptors and are useful in the diagnosis and treatment of stress related disorders such as post traumatic stress disorder (PTSD) as well as depression and anxiety.

The invention further encompasses methods for treating mammals, such as, for example, humans and companion animals (i.e., cats and dogs) suffering from PTSD, depression, and/or anxiety. Such methods comprise administering to a patient mammal an amount effective of a compound of Formula I to relieve the depression, anxiety or PTSD.

DETAILED DESCRIPTION OF THE INVENTION

In addition to the compounds of Formula I above, the invention provides compounds encompassed by Formula II:

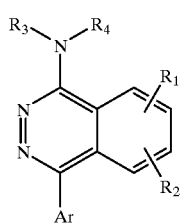

II wherein
Ar is phenyl, 1- or 2-naphthyl, 2-, 3-, or 4-pyridinyl, 2- or 3-thienyl, 4- or 5-pyrimidinyl, each of which is mono-, di-, or trisubstituted with halogen, hydroxy, $C_1$–$C_6$ alkyl, $C_1$–$C_6$ alkoxy with the proviso that at least one of the positions on Ar ortho to the point of attachment to the phthalazinamine ring is substituted;

$R_1$ and $R_2$ are the same or different and represent
hydrogen, $C_1$–$C_6$ alkyl, halogen, hydroxy, $C_1$–$C_6$ alkoxy, NH₂, NH($C_1$–$C_6$ alkyl), N($C_1$–$C_6$ alkyl)₂, NO₂, cyano, trifluoromethyl; and $R_3$ and $R_4$ are the same or different and represent
hydrogen, $C_1$–$C_6$ alkyl optionally substituted with halogen, hydroxy, or $C_1$–$C_6$ alkoxy; or
aryl($C_1$–$C_6$)alkyl, where aryl is phenyl, 1- or 2-naphthyl, 2-, 3-, or 4-pyridinyl, 2- or 3-thienyl or 2-, 4-, or 5-pyrimidinyl, each of which is optionally mono- or disubstituted with halogen, hydroxy, $C_1$–$C_6$ alkyl, $C_1$–$C_6$ alkoxy; or $C_1$–$C_6$ alkyl-Y—$R_5$, wherein Y is O, S NH, N($C_1$–$C_6$ alkyl), and $R_5$ is hydrogen or $C_1$–$C_6$ alkyl.

In preferred compounds of Formula II, $R_3$ and $R_4$ are not both hydrogen simultaneously. Preferred compounds of formula II are those where $R_3$ and $R_4$ independently represent $C_1$–$C_6$ alkyl optionally substituted with halogen, hydroxy, or $C_1$–$C_6$ alkoxy, Ar is phenyl that is mono-, di-, or trisubstituted with halogen, hydroxy, $C_1$–$C_6$ alkyl, or $C_1$–$C_6$ alkoxy, with the proviso that at least one of the positions on the phenyl group ortho to the point of attachment to the phthalazinamine ring is substituted. More preferred compounds of Formula II are those where $R_1$ and $R_2$ are independently hydrogen or lower alkyl, most preferably hydrogen or $C_1$–$C_3$ alkyl; and Ar is phenyl that is trisubstituted with $C_1$–$C_6$ alkyl, with the proviso that at least one of the positions on the phenyl group ortho to the point of attachment to the phthalazinamine ring is substituted. Most preferred compounds of Formula II are those where $R_1$ and $R_2$ are hydrogen; and $R_3$ and $R_4$ independently represent $C_1$–$C_6$ alkyl optionally substituted with halogen, hydroxy, or $C_1$–$C_6$ alkoxy, Ar is phenyl that is trisubstituted in the 2, 4, and 6 positions (para and both ortho positions relative to the point of attachment to the phthalazinamine ring) with $C_1$–$C_3$ alkyl, most preferably methyl. Particularly preferred compounds of Formula II are those where $R_3$ and $R_4$ are independently hydrogen or $C_1$–$C_4$ alkyl, e.g., methyl, ethyl, propyl, butyl, or cyclopropylmethyl, provided that not both $R_3$ and $R_4$ are hydrogen simultaneously.

The invention also provides compounds of formula III:

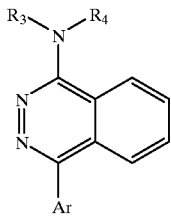

III wherein
- Ar is phenyl, 1- or 2-naphthyl, 2-, 3-, or 4-pyridinyl, 2- or 3-thienyl, 4- or 5-pyrimidinyl, each of which is mono-, di-, or trisubstituted with halogen, hydroxy, $C_1$–$C_6$ alkyl, $C_1$–$C_6$ alkoxy with the proviso that at least one of the positions on Ar ortho to the point of attachment to the phthalazinamine ring is substituted; and
- $R_3$ and $R_4$ are the same or different and represent hydrogen, $C_1$–$C_6$ alkyl optionally substituted with halogen, hydroxy, or $C_1$–$C_6$ alkoxy; or aryl($C_1$–$C_6$)alkyl, where aryl is phenyl, 1- or 2-naphthyl, 2-, 3-, or 4-pyridinyl, 2- or 3-thienyl or 2-, 4-, or 5-pyrimidinyl, each of which is optionally mono- or disubstituted with halogen, hydroxy, $C_1$–$C_6$ alkyl, $C_1$–$C_6$ alkoxy; or $C_1$–$C_6$ alkyl-Y—$R_5$, wherein Y is O, S NH, N($C_1$–$C_6$ alkyl), and $R_5$ is hydrogen or $C_1$–$C_6$ alkyl.

In preferred compounds of Formula III, $R_3$ and $R_4$ are not both hydrogen simultaneously. Preferred compounds of formula III are those where $R_3$ and $R_4$ independently represent $C_1$–$C_6$ alkyl optionally substituted with halogen, hydroxy, or $C_1$–$C_6$ alkoxy, Ar is phenyl that is mono-, di-, or trisubstituted with halogen, hydroxy, $C_1$–$C_6$ alkyl, or $C_1$–$C_6$ alkoxy, with the proviso that at least one of the positions on the phenyl group ortho to the point of attachment to the phthalazinamine ring is substituted. Most preferred compounds of Formula III are those where $R_3$ and $R_4$ independently represent $C_1$–$C_6$ alkyl optionally substituted with halogen, hydroxy, or $C_1$–$C_6$ alkoxy, Ar is phenyl that is trisubstituted in the 2, 4, and 6 positions (para and both ortho positions relative to the point of attachment to the phthalazinamine ring) with $C_1$–$C_3$ alkyl, most preferably methyl. Particularly preferred compounds of Formula III are those where $R_3$ and $R_4$ are independently hydrogen or $C_1$–$C_4$ alkyl, e.g., methyl, ethyl, propyl, butyl, or cyclopropylmethyl, provided that not both $R_3$ and $R_4$ are hydrogen simultaneously.

The invention provides compounds of formula IV

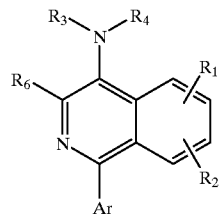

IV wherein
- Ar is phenyl, 1- or 2-naphthyl, 2-, 3-, or 4-pyridinyl, 2- or 3-thienyl, 4- or 5-pyrimidinyl, each of which is mono-, di-, or trisubstituted with halogen, hydroxy, $C_1$–$C_6$ alkyl, $C_1$–$C_6$ alkoxy with the proviso that at least one of the positions on Ar ortho to the point of attachment to the isoquinolinamine ring is substituted;
- $R_1$ and $R_2$ are the same or different and represent hydrogen, $C_1$–$C_6$ alkyl, halogen, hydroxy, $C_1$–$C_6$ alkoxy, $NH_2$, $NH(C_1$–$C_6$ alkyl), $N(C_1$–$C_6$ alkyl)$_2$, $NO_2$, cyano, trifluoromethyl;
- $R_3$ and $R_4$ are the same or different and represent hydrogen, $C_1$–$C_6$ alkyl optionally substituted with halogen, hydroxy, or $C_1$–$C_6$ alkoxy; or aryl($C_1$–$C_6$)alkyl, where aryl is phenyl, 1- or 2-naphthyl, 2-, 3-, or 4-pyridinyl, 2- or 3-thienyl or 2-, 4-, or 5-pyrimidinyl, each of which is optionally mono- or disubstituted with halogen, hydroxy, $C_1$–$C_6$ alkyl, $C_1$–$C_6$ alkoxy; or $C_1$–$C_6$ alkyl-Y—$R_5$, wherein Y is O, S NH, N($C_1$–$C_6$ alkyl), and $R_5$ is hydrogen or $C_1$–$C_6$ alkyl; and
- $R_6$ is hydrogen or $C_1$–$C_6$ alkyl.

In preferred compounds of Formula IV, $R_3$ and $R_4$ are not both hydrogen simultaneously. Preferred compounds of Formula IV are those where $R_3$ and $R_4$ independently represent $C_1$–$C_6$ alkyl optionally substituted with halogen, hydroxy, or $C_1$–$C_6$ alkoxy, Ar is phenyl that is mono-, di-, or trisubstituted with halogen, hydroxy, $C_1$–$C_6$ alkyl, or $C_1$–$C_6$ alkoxy, with the proviso that at least one of the positions on the phenyl group ortho to the point of attachment to the isoquinolinamine ring is substituted. Most preferred compounds of Formula IV are those where $R_3$ and $R_4$ independently represent $C_1$–$C_6$ alkyl optionally substituted with halogen, hydroxy, or $C_1$–$C_6$ alkoxy, Ar is phenyl that is trisubstituted in the 2, 4, and 6 positions (para and both ortho positions relative to the point of attachment to the isoquinolinamine ring) with $C_1$–$C_3$ alkyl, most preferably methyl. Particularly preferred compounds of Formula IV are those where $R_3$ and $R_4$ are independently hydrogen or $C_1$–$C_4$ alkyl, e.g., methyl, ethyl, propyl, butyl, or cyclopropylmethyl, provided not both $R_3$ and $R_4$ are hydrogen simultaneously.

The invention also provides compounds of formula V:

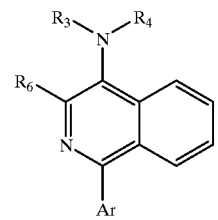

V wherein
- Ar is phenyl, 1- or 2-naphthyl, 2-, 3-, or 4-pyridinyl, 2- or 3-thienyl, 4- or 5-pyrimidinyl, each of which is mono-, di-, or trisubstituted with halogen, hydroxy, $C_1$–$C_6$ alkyl, $C_1$–$C_6$ alkoxy with the proviso that at least one of the positions on Ar ortho to the point of attachment to the isoquinolinamine ring is substituted;

$R_3$ and $R_4$ are the same or different and represent hydrogen, $C_1$–$C_6$ alkyl optionally substituted with halogen, hydroxy, or $C_1$–$C_6$ alkoxy; or aryl($C_1$–$C_6$)alkyl, where aryl is phenyl, 1- or 2-naphthyl, 2-, 3-, or 4-pyridinyl, 2- or 3-thienyl or 2-, 4-, or 5-pyrimidinyl, each of which is optionally mono- or disubstituted with halogen, hydroxy, $C_1$–$C_6$ alkyl, $C_1$–$C_6$ alkoxy; or $C_1$–$C_6$ alkyl-Y—$R_5$, wherein Y is O, S NH, N($C_1$–$C_6$ alkyl), and $R_5$ is hydrogen or $C_1$–$C_6$ alkyl; and $R_6$ is hydrogen or $C_1$–$C_6$ alkyl.

In preferred compounds of Formula V, $R_3$ and $R_4$ are not both hydrogen simultaneously. Preferred compounds of formula V are those where $R_3$ and $R_4$ independently represent $C_1$–$C_6$ alkyl optionally substituted with halogen, hydroxy, or $C_1$–$C_6$ alkoxy, Ar is phenyl that is mono-, di-, or trisubstituted with halogen, hydroxy, $C_1$–$C_6$ alkyl, or $C_1$–$C_6$ alkoxy, with the proviso that at least one of the positions on the phenyl group ortho to the point of attachment to the isoquinolinamine ring is substituted. Most preferred compounds of Formula V are those where $R_3$ and $R_4$ independently represent $C_1$–$C_6$ alkyl optionally substituted with halogen, hydroxy, or $C_1$–$C_6$ alkoxy, Ar is phenyl that is trisubstituted in the 2, 4, and 6 positions (para and both ortho positions relative to the point of attachment to the isoquinolinamine ring) with $C_1$–$C_3$ alkyl, most preferably methyl. Particularly preferred compounds of Formula V are those where $R_3$ and $R_4$ are independently hydrogen or $C_1$–$C_4$ alkyl, e.g., methyl, ethyl, propyl, butyl, or cyclopropylmethyl, provided not both $R_3$ and $R_4$ are hydrogen simultaneously.

The invention also encompasses intermediates for preparing compounds of Formula I. Among these intermediates are compounds of Formula VI:

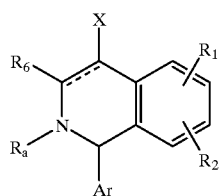

VI wherein

X is $NH_2$ or $NO_2$;

$R_1$, $R_2$, and $R_6$, are as defined above for Formula I;

$R_a$ is hydrogen or $R_bO_2C$— where $R_b$ represents $C_1$–$C_6$ alkyl; and

Ar is phenyl, 1- or 2-naphthyl, 2-, 3-, or 4-pyridinyl, 2- or 3-thienyl, 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the isoquinolinamine ring is substituted.

Preferred Ar groups are 2,4,6-tri($C_1$–$C_6$)alkylphenyl groups, most preferably 2,4,6-trimethylphenyl.

The invention further encompasses intermediates of Formula VII:

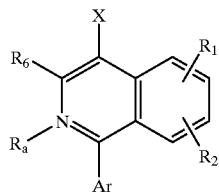

VII wherein

X is $NH_2$ or $NO_2$;

$R_1$, $R_2$, and $R_6$, are as defined above for Formula I;

$R_a$ is hydrogen or $R_bO_2C$— where $R_b$ represents $C_1$–$C_6$ alkyl; and

Ar is phenyl, 1- or 2-naphthyl, 2-, 3-, or 4-pyridinyl, 2- or 3-thienyl, 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the isoquinolinamine ring is substituted.

Preferred Ar groups are 2,4,6-tri($C_1$–$C_6$)alkylphenyl groups, most preferably 2,4,6-trimethylphenyl.

The invention further encompasses intermediates of Formula VIII:

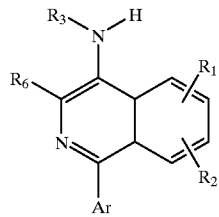

VIII wherein $R_1$, $R_2$, $R_3$, and $R_6$, are as defined above for Formula I; and Ar is phenyl, 1- or 2-naphthyl, 2-, 3-, or 4-pyridinyl, 2- or 3-thienyl, 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the isoquinolinamine ring is substituted.

Preferred Ar groups are 2,4,6-tri($C_1$–$C_6$)alkylphenyl groups, most preferably 2,4,6-trimethylphenyl.

Also encompassed by the invention are intermediates useful for preparing phthalazinamines of the invention. Thus, compounds of Formula IX are within the invention:

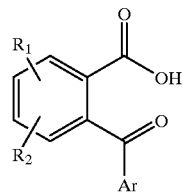

IX wherein $R_1$, and $R_2$ are as defined above for Formula I; and

Ar is phenyl, 1- or 2-naphthyl, 2-, 3-, or 4-pyridinyl, 2- or 3-thienyl, 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the benzene ring is substituted.

Preferred Ar groups are 2,4,6-tri($C_1$–$C_6$)alkylphenyl groups, most preferably 2,4,6-trimethylphenyl groups.

The invention also encompasses compounds of Formula X:

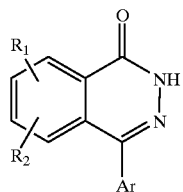

$R_1$, and $R_2$ are as defined above for Formula I; and

Ar is phenyl, 1- or 2-naphthyl, 2-, 3-, or 4-pyridinyl, 2- or 3-thienyl, 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the phthalazinone ring is substituted.

Preferred Ar groups are 2,4,6-tri($C_1$–$C_6$)alkylphenyl groups, most preferably 2,4,6-trimethylphenyl.

The invention also encompasses compounds of Formula XI:

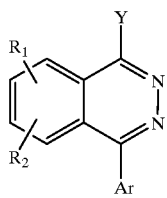

$R_1$ and $R_2$ are as defined above for Formula I;

Y is a halogen, preferably chloride or bromide; and

Ar is phenyl, 1- or 2-naphthyl, 2-, 3-, or 4-pyridinyl, 2- or 3-thienyl, 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the phthalazinamine ring is substituted.

Preferred Ar groups are 2,4,6-tri($C_1$–$C_6$)alkylphenyl groups, most preferably 2,4,6-trimethylphenyl.

Representative compounds of the present invention, which are encompassed by Formula I, include, but are not limited to the compounds in Table I and their pharmaceutically acceptable salts. Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

When a compound of formula I is obtained as a mixture of enantiomers these may be separated by conventional methods such as crystallization in the presence of a resolving agent, or chromatography, for example, using a chiral HPLC column.

In the compounds of the invention, the Ar group is preferably a phenyl group that is mono-, di-, or trisubstituted with halogen, hydroxy, $C_1$–$C_6$ alkyl, or $C_1$–$C_6$ alkoxy, with the proviso that at least one of the positions on the phenyl group ortho to the point of attachment to the isoquinolinamine or phthalazinamine ring is substituted. Where Ar is phenyl, the carbon atom by which the phenyl group is attached to the isoquinolinamine or phthalazinamine ring is defined as the 1-position. Thus, the positions ortho to the point of attachment are the 2 and 6 positions, and the para position is the 4-position of the phenyl group.

By the terms ($C_1$–$C_6$)alkyl and lower alkyl is meant straight and branched chain alkyl groups having from 1–6 carbon atoms as well as cyclic alkyl groups such as, for example, cyclopropyl, cyclobutyl, or cyclohexyl. Specific examples of such alkyl groups are methyl, ethyl, propyl, isopropyl, n-butyl, isobutyl, tert-butyl, sec-butyl, neopentyl and n-pentyl. Preferred $C_1$–$C_6$ alkyl groups are methyl, ethyl, propyl, butyl or cyclopropylmethyl.

By the terms ($C_1$–$C_6$)alkoxy and lower alkoxy is meant, straight and branched chain alkoxy groups having from 1–6 carbon atoms.

By hydroxy $C_1$–$C_6$ alkyl is meant a $C_1$–$C_6$ alkyl group carrying a terminal hydroxy moiety.

By $C_1$–$C_6$ alkoxy $C_1$–$C_6$ alkyl is meant a group of the formula —$(CH_2)_xO(CH_2)_yCH_3$, where x and y independently represent integers of from 1–6.

By the term $C_1$–$C_6$ alkenyl is meant straight or branched chain hydrocarbon groups having from 1–6 carbon atoms and at least one double bond.

By halogen, halo, or halide is meant fluorine, chlorine, bromine and iodine substituents.

By aryl($C_1$–$C_6$)alkyl is meant aryl groups attached to the parent group by a straight or branched chain alkyl group having 1–6 carbon atoms. The aryl groups include phenyl, 1- or 2-naphthyl, 2-, 3-, or 4-pyridinyl, 2- or 3-thienyl or 2-, 4-, or 5-pyrimidinyl and are optionally substituted with up to two groups selected from halogen, hydroxy, ($C_1$–$C_6$)alkyl, and ($C_1$–$C_6$)alkoxy.

Representative examples of compounds according to the invention are shown in Table 1 below.

TABLE 1[1]

| Compound No. | |
|---|---|
| 1 | 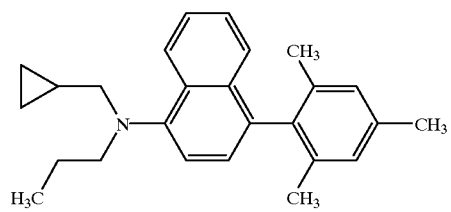 |

TABLE 1¹-continued

Compound
No.

2

The pharmaceutical utility of compounds of this invention are indicated by the following assay for CRF receptor activity.

Assay for CRF Receptor Binding Activity

CRF receptor binding is performed using a modified version of the assay described by Grigoriadis and De Souza (Biochemical, Pharmacological, and Autoradiographic Methods to Study Corticotropin-Releasing Factor Receptors. *Methods in Neurosciences,* Vol. 5, 1991). Membrane pellets containing CRF receptors are resuspended in 50 mM Tris buffer pH 7.7 containing 10 mM $MgCl_2$ and 2 mM EDTA and centrifuged for 10 minutes at 48000 g. Membranes are washed again and brought to a final concentration of 1500 mg/ml in binding buffer (Tris buffer above with 0.1% BSA, 15 mM bacitracin and 0.01 mg/ml aprotinin.). For the binding assay, 100 ml of the membrane preparation is added to 96 well microtube plates containing 100 ml of $^{125}$I-CRF (SA 2200 Ci/mmol, final concentration of 100 pM) and 50 ml of drug. Binding is carried out at room temperature for 2 hours. Plates are then harvested on a Brandel 96 well cell harvester and filters are counted for gamma emissions on a Wallac 1205 Betaplate liquid scintillation counter. Non specific binding is defined by 1 mM cold CRF. $IC_{50}$ values are calculated with the non-linear curve fitting program RS/1 (BBN Software Products Corp., Cambridge, Mass.).

The compounds of the invention typically have binding affinities, expressed as $IC_{50}$ values, of from about 0.5 nanomolar (nM) to about 10 micromolar ($\mu$M).

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin. Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, For example beeswax, hard paraffin or cetyl alcohol. Sweetening agents such as those set forth above, and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A representative illustration of methods suitable for the preparation of compounds of the present invention is shown in Schemes I and II. Those having skill in the art will recognize that the starting materials may be varied and additional steps employed to produce compounds encompassed by the present invention. For example, in certain situations, protection of reactive moieties such as amino groups, will be required.

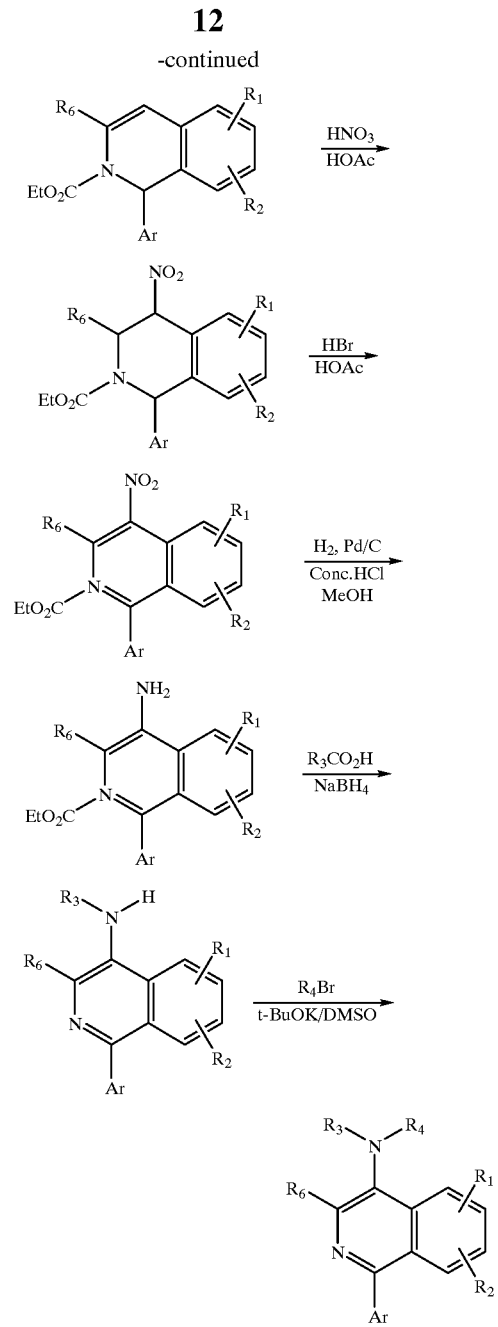

wherein Ar, $R_1$, $R_2$, $R_3$, $R_4$, and $R_6$ are as defined as above for Formula I.

Scheme I

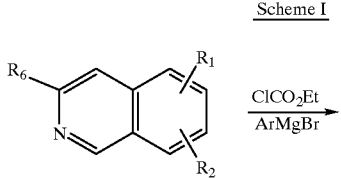

Scheme II

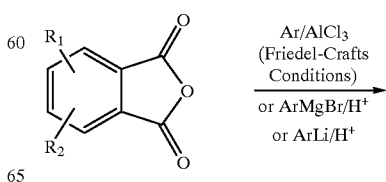

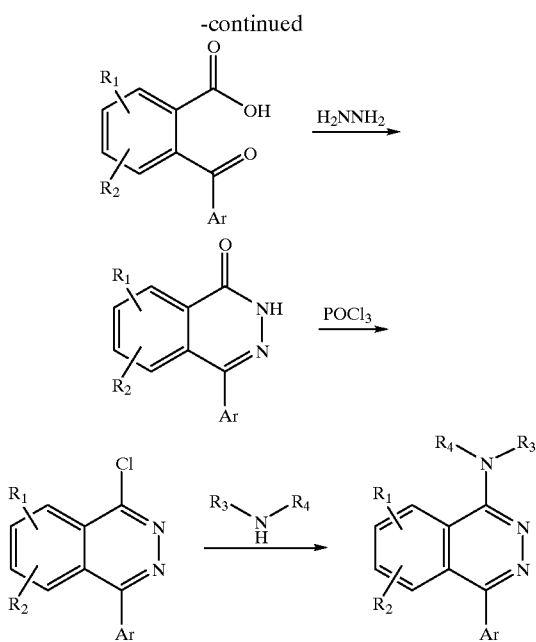

In the above scheme, $R_1$-$R_4$, $R_6$, W and Ar carry the definitions set forth above for Formula I.

The disclosures in this application of all articles and references, including patents, are incorporated herein by reference.

The invention is illustrated further by the following examples which are not to be construed as limiting the invention in scope or spirit to the specific procedures and compounds described in them.

EXAMPLE 1

A. Ethyl 1-(2,4,6-trimethylphenyl)-1,2-dihydro-2-isoquinolinecarboxylate

A solution of 2-mesitylmagnesium bromide in THF (1.0 M, 11 mL; 11 mmol) was added to an ice-cold solution of isoquinoline (1.3 g, 10 mmol) in THF (10 ml). After 5 minutes, ethyl chloroformate was added slowly dropwise and the mixture was further stirred at 0° C. for 10 min before quenched by saturated $NH_4CL$ solution. The mixture was poured into 0.5 N hydrochloric acid and extracted twice with ethyl ether. Combined organics were washed with brine, dried over $Na_2SO_4$, filtered, and concentrated in vacuo to give 3.58 g of titled compound (quantitative) as an oil which was used in the next reaction without further purification.

B. Ethyl 4-nitro-1(2,4,6-triethylphenyl)-1,2-dihydro-2-isquinolinecarboxylate

To a solution of the product of step A (1.6 g, 5.0 mmol) in acetic acid (8 mL) was cautiously added nitric acid (90%, 0.35 mL, 7.5 mmol) with external cooling. After the addition, the mixture was allowed to worm to room temperature and further stirred for 2.5 h. Resulting yellow suspension was filtered and the crystalline solid collected was washed with methanol and air-dried to give 0.83 g of the dihydronitroisoquinoline, m.p. 171° C. (dec.)

C. 4-Nitro-1-(2,4,6-trimethylphenyl)-isoquinoline

Hydrobromic acid (3.0 M in HOAc, 1 mL) was added to a suspension of the dihydronitroisoquinoline (0.83 g) in glacial HOAc (2 mL). The mixture was heated to 100° C. for 1 day with occasional addition of more hydrobromic acid solution (3 mL overall). After the reaction, the mixture was allowed to cool to room temperature, concentrated in vacuo, diluted by water, and extracted twice with ethyl ether. Combined organics were washed by saturated $NaHCO_3$ solution, dried over $Na_2SO_4$, filtered, concentrated in vacuo, and chromatographed on silica gel (5% to 10% ethyl acetate in hexane) to give 234 mg of nitroisoquinoline (35%) as solids, along with 95 mg of 4-bromo -1(2,4,6-trimethylphenyl)isoquinoline (13%).

D. 4-Amino-1-(2,4,6-trimethylphenyl)-isoquinoline

A solution of nitroisoquinoline (210 mg, 0.72 mmol) in MeOH (10 mL) was placed in Parr hydrogenation bottle, to which was added conc. HCl (ca. 0.1 ml) and 10% palladium on carbon (ca. 10 mg). The mixture was shaken under 50 psi of hydrogen pressure fir 4 h and filtered on celite. The filtrate was diluted by 1N NaOH and extracted 3 times with $CH_2Cl_2$, and combined extracts were dried over $Na_2SO_4$, filtered, concentrated in vacuo, and chromatographed on silica gel (33% to 67% ethyl acetate in hexane) to give 135 mg of the aminoisoquinoline as an oil.

E. N-Propyl-1-(2,4,6-trimethylphenyl)-4-isoquinolinamine

The aminoisoquinoline (50 mg, 0.19 mmol) was dissolved in propionic acid (0.5 mL) and $NaBH_4$ (30 mg) was added in portions as a solid. After 5 min, the mixture was heated to 100° C. for 45 minutes before cooled back to room temperature. The mixture was diluted by 1N HCl and vigorously stirred for 4 min, basified by cold 1N NaOH, and extracted 3 times with $CH_2Cl_2$. Combined extracts were dried over $Na_2SO_4$, filtered, and concentrated in vacuo to give 55 mg of the title compound as an oil which was used in the next reaction without further purification.

F. N-cyclopropylmethyl-N-propyl-1-(2,4,6-trimethylphenyl)-4-isoquinolinamine (Compound 1)

To a solution of the product of step E (72 mg, 9.24 mmol) in DMSO (0.7 mL) was added potassium t-butoxide (40 mg, 0.36 mmol), followed by slow dropwise addition of bromomethylcyclopropane (0.028 mL, 0.3 mmol). The mixture was stirred at room temperature for 1 h, diluted by aqueous $NH_4Cl$, and extracted twice with 50% ethyl ether in hexane. Combined organics were dried over $Na_2SO_4$, filtered, concentrated, and chromatographed on silica gel (6% to 10% ethyl acetate in hexane) to give 62 mg of the title compound as an oil $^1H$ NMR (CDCl$_3$): δ0.10 (m, 2H), 0.50 (m,2H), 0.78 (t,3H), 1.00 (m, 1H), 1.50 (q,2H), 186 (s, 6H), 2.38 (s, 3H), 2.45 (d, 2H), 2.56 (t, 2H), 4.07 (s, 2H), 6.98 (s, 2H), 7.42 (5, 1H), 7.52 (d,1H), 7.66 (t, 1H), 8.48 (d, 1H), 8.53 (s 1H)ppm.

The following compounds are prepared essentially according to procedures set forth above in Example 1.

EXAMPLE 2
N-Cyclopropylmethyl-N-ethyl-1-(2,4,6-trimethylphenyl)-4-isoquinolinamine
(Compound 3).

EXAMPLE 3
N-benzyl-N-propyl-1-(2,4,6-trimethylphenyl)-4-isoquinolinamine (Compound 4).

EXAMPLE 4
N-Cyclopropylmethyl-N-(2-methoxyethyl)-1-(2,4,6-trimethylphenyl)-4-isoquinolinamine
(Compound 5).

EXAMPLE 5
N,N-Dipropyl-1-(2,4,6-trimethylphenyl)-4-isoquinolinamine (Compound 6).

EXAMPLE 6
N-Cyclopropylmethyl-N-propyl-3-methyl-1-(2,4,6-trimethylphenyl)-4-isoquinolinamine
(Compound 7).

EXAMPLE 7

A. 2-(2,4,6-Trimethylbenzoyl)-benzoic acid

Aluminum chloride (60 g, 0.45 mol) was added in portions to a solution of phthalic anhydride (30 g, 0.20 mol) and mesitylene (40 mL) in 150 mL of 1,2-dichloroethane at 0° C. the reaction mixture was stirred at room temperature for 2 hours, then poured into ice-water. The mixture was acidified with 37% hydrochloric acid and extracted with ether. The ether extract was washed with 1 N hydrochloric acid, water, dried and concentrated to give 59 g of the title compound as white solids which was used in the next reaction without further purification.

B. 4-(2,4,6-Trimethylphenyl)-1(2H)phthalazinone

A mixture of 2-(2,4,6-trimethylbenzoyl-benzoic acid (5.0 g, 18.7 mmol) and hydrazine hydrate (2 mL) in 15 mL of EtOH was stirred at reflux for 8. hours. The solvent was then removed from the mixture. The residue was heated to melt for about 10 minutes and then solidified by cooling. The resulting yellow solids were triturated with ether and filtered. The solid was washed with 1 N NaOH and water, and dried to give 1.8 g of titled compound as yellow solids, m.p. 259–62° C.

C. 4-(2,4,6-Trimethylphenyl)-4-chloro-phthalazine

A solution of 4-(2,4,6-Trimethylphenyl)-1(2H) phthalazinone (1.0 g) in 5 mL of $POCl_3$ was heated at 80° C. for 2 hours. The excess $POCl_3$ was removed under reduce pressure. The resulting residue was dissolved in ethyl acetate and washed with $NaHCO_3$ solution and water. The ethyl acetate solution was then dried over $Na_2SO_4$ and concentrated to a yellow solid which was used in the next reaction without further purification.

D. N-Cyclopropylmethyl-N-propyl-4-(2,4,6-trimethylphenyl)-1-phthalazinamine (Compound 2)

A mixture of the product of step C (100 mg), N-propyl-N-cyclopropylmethylamine (0.5 mL) and in 1 mL of toluene was heated at 100° C. overnight. The mixture was cooled and concentrated. The residue was purified through silica gel column chromatography to give 40 mg of the title compound as an oil. $^1$H NMR ($CDCl_3$): δ0.08 (q, 2H), 0.50 (q 2H), 0.95 (t, 3H), 1.20 (m, 1H), 1.76 9 m, 2H), 1.92 (s, 6H), 2.36)s, 3H), 3.45 (d, 2H), 3.68 (m, 2H), 6.90 (s, 2H), 7.36 (d, 1H), 7.64 (t, 1H), 7.74 (t, 1H), 8.19 (d, 1H)ppm.

The following compounds are prepared essentially according to procedures set forth above in EXAMPLE 7.

EXAMPLE 8
N-Cyclopropylmethyl-N-ethyl-4-(2,4,6-trimethyphenyl)-1-phthalazinamine (Compound 8).

EXAMPLE 9
N-Cyclopropylmethyl-N-methyl-4-(2,4,6-trimethyphenyl)-1-phthalazinamine (Compound 9).

EXAMPLE 10
N-Cyclopropylmethyl-N-(2-methoxyethyl)-4-(2,4,6-trimethyphenyl)-1-phthalazinamine (Compound 10).

EXAMPLE 11
N-Benzyl-N-ethyl-4-(2,4,6-trimethyphenyl)-1-phthalazinamine (Compound 11).

EXAMPLE 12
N-(2'-Chlorophenylmethyl-N-ethyl-4-(2,4,6-trimethyphenyl) -1-phthalazinamine (Compound 12).

EXAMPLE 13
N-(4'-Chlorophenylmethyl-N-ethyl-4-(2,4,6-trimethyphenyl) -1-phthalazinamine (Compound 13).

EXAMPLE 14
N-(2'-Tolymethyl)-N-ethyl-4-(2,4,6-trimethyphenyl)-1-phthalazinamine (Compound 14).

EXAMPLE 15
N-(2'-Methoxyphenylmethyl)-N-ethyl-4-(2,4,6-trimethyphenyl)-1-phthalazinamine (Compound 15).

EXAMPLE 16
N-(2'-Pyridylmethyl)-N-ethyl-4-(2,4,6-trimethyphenyl)-1phthalazinamine (Compound 16).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

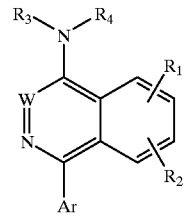

or the pharmaceutically acceptable salts thereof, wherein

Ar is phenyl, 1- or 2-naphthyl, 2-, 3-, or 4-pyridinyl, or 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the nitrogen-containing aromatic ring is substituted;

$R_1$ and $R_2$ are the same of different and represent hydrogen, $C_1$–$C_6$ alkyl, halogen, hydroxy, $C_1$–$C_6$ alkoxy, $NH_2$, $NH(C_1$–$C_6$alkyl), $N(C_1$–$C_6$alkyl)$_2$, $NO_2$, cyano, or trifluoromethyl;

$R_3$ and $R_4$ are the same or different and represent hydrogen, $C_1$–$C_6$ alkyl optionally substituted with halogen, hydroxy, or $C_1$–$C_6$ alkoxy; aryl($C_1$–$C_6$)alkyl, where aryl is phenyl, 1- or 2-naphthyl, 2-, 3-, or 4-pyridinyl, 2- or 3-thienyl or 2-, 4-, or 5-pyrimidinyl, each of which is optionally mono- or disubstituted with halogen, hydroxy, $C_1$–$C_6$ alkyl, $C_1$–$C_6$ alkoxy; or $c_1$–$C_6$ alkyl-Y—$R_5$, wherein Y is O, S, NH, or $N(C_1$–$C_6$ alkyl), and $R_5$ is hydrogen or $C_1$–$C_6$ alkyl; and W is N or C—$R_6$, wherein $R_6$ is hydrogen or $C_1$–$C_6$ alkyl.

2. A compound of the formula:

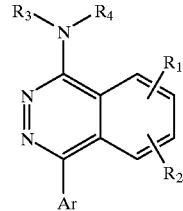

or the pharmaceutically acceptable salts thereof wherein

Ar is phenyl, 1- or 2-naphthyl, 2-, 3-, or 4-pyridinyl, 2- or 3-thienyl, or 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the phthalazinamine ring is substituted;

$R_1$ and $R_2$ are the same or different and represent hydrogen, $C_1$–$C_6$ alkyl, halogen, hydroxy, $C_1$–$C_6$ alkoxy, $NH_2$, $NH(C_1$–$C_6$ alkyl), $N(C_1$–$C_6$ alkyl)$_2$, $NO_2$, cyano, trifluoromethyl; and $R_3$ and $R_4$ are the same or different and represent hydrogen, $C_1$–$C_6$ alkyl optionally substituted with halogen, hydroxy, or $C_1$–$C_6$ alkoxy, provided that not both $R_3$ and $R_4$ are hydrogen simultaneously; or aryl($C_1$–$C_6$)alkyl, where aryl is phenyl, 1- or 2-naphthyl, 2-, 3-, or 4-pyridinyl, 2- or 3-thienyl or 2-, 4-, or 5-pyrimidinyl, each of which is optionally mono- or disubstituted with halogen, hydroxy, $C_1$–$C_6$ alkyl, $C_1$–$C_6$ alkoxy; or $C_1$–$C_6$ alkyl-Y—$R_5$, wherein Y is O, S NH, N($C_1$–$C_6$ alkyl), and $R_5$ is hydrogen or $C_1$–$C_6$ alkyl.

3. A compound according to claim 2, wherein Ar is phenyl mono-, di-, or trisubstituted with halogen, hydroxy, $C_1$–$C_6$ alkyl, or $C_1$–$C_6$ alkoxy, with the proviso that at least one of the positions on the phenyl group ortho to the point of attachment to the phthalazinamine ring is substituted.

4. A compound according to claim 3, wherein $R_1$ and $R_2$ are hydrogen.

5. A compound according to claim 4, wherein $R_3$ and $R_4$ are independently hydrogen or $C_1$–$C_4$ alkyl.

6. A compound of the formula:

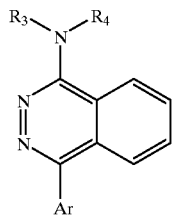

or the pharmaceutically acceptable salts thereof wherein

Ar is phenyl mono, di-, or trisubstituted with halogen, hydroxy, $C_1$–$C_6$ alkyl, or $C_1$–$C_6$ alkoxy, with the proviso that at least one of the positions on Ar ortho to the point of attachment to the phthalazinamine ring is substituted; and $R_3$ and $R_4$ are the same or different and represent
hydrogen, $C_1$–$C_6$ alkyl optionally substituted with halogen, hydroxy, or $C_1$–$C_6$ alkoxy; or
aryl($C_1$–$C_6$)alkyl, where aryl is phenyl, 1- or 2-naphthyl, 2-, 3-, or 4-pyridinyl, 2- or 3-thienyl or 2-, 4-, or 5-pyrimidinyl, each of which is optionally mono - or disubstituted with halogen, hydroxy, $C_1$–$C_6$ alkyl, $C_1$–$C_6$ alkoxy; or $C_1$–$C_6$ alkyl-Y—$R_5$, wherein Y is O, S NH, N($C_1$–$C_6$ alkyl), and $R_5$ is hydrogen or $C_1$–$C_6$ alkyl.

7. A compound according to claim 6, wherein Ar is phenyl trisubstituted in the 2, 4, and 6 positions relative to the point of attachment to the phthalazinamine ring with $C_1$–$C_3$ alkyl.

8. A compound according to claim 7, wherein Ar is 2,4,6-trimethylphenyl.

9. A compound of the formula:

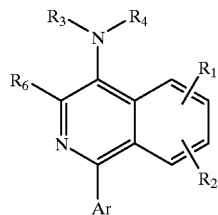

or a pharmaceutically acceptable salt thereof wherein

Ar is phenyl, 1- or 2-naphthyl, 2-, 3-, or 4-pyridinyl, or 4- or 5-pyrimidinyl, each of which is mono-, di-, or trisubstituted with halogen, hydroxy, $C_1$–$C_6$ alkyl, or $C_1$–$C_6$ alkoxy with the proviso that at least one of the positions on Ar ortho to the point of attachment to the isoquinolinamine ring is substituted;

$R_1$ and $R_2$ are the same or different and represent hydrogen, $C_1$–$C_6$ alkyl, halogen, hydroxy, $C_1$–$C_6$ alkoxy, $NH_2$, NH($C_1$–$C_6$ alkyl), N($C_1$–$C_6$ alkyl)$_2$, $NO_2$, cyano, or trifluoromethyl; and $R_3$ and $R_4$ are the same or different and represent
hydrogen, $C_1$–$C_6$ alkyl optionally substituted with halogen, hydroxy, or $C_1$–$C_6$ alkoxy; or
aryl($C_1$–$C_6$)alkyl, where aryl is phenyl, 1- or 2-naphthyl, 2-, 3-, or 4-pyridinyl, 2- or 3-thienyl or 2-, 4-, or 5-pyrimidinyl, each of which is optionally mono- or disubstituted with halogen, hydroxy, $C_1$–$C_6$ alkyl, $C_1$–$C_6$ alkoxy; or $C_1$–$C_6$ alkyl-Y—$R_5$, wherein Y is O, S, NH, or N($C_1$–$C_6$ alkyl), and $R_5$ is hydrogen or $C_1$–$C_6$ alkyl; and $R_6$ is hydrogen or $C_1$–$C_6$ alkyl.

10. A compound according to claim 9, wherein Ar is phenyl or 1- or 2-naphthyl, each of which is mono-, di-, or trisubstituted with halogen, hydroxy, $C_1$–$C_6$ alkyl, or $C_1$–$C_6$ alkoxy, with the proviso that at least one of the positions on the Ar group ortho to the point of attachment to the isoquinolinamine ring is substituted.

11. A compound according to claim 10, wherein at least one of $R_1$ and $R_2$ are hydrogen.

12. A compound according to claim 11, wherein $R_3$ and $R_4$ are independently hydrogen or $C_1$–$C_4$ alkyl, which is unsubstituted or substituted with halogen, hydroxy, or alkoxy.

13. A compound of the formula:

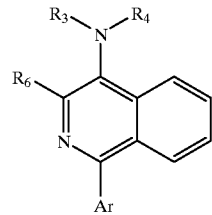

or a pharmaceutically acceptable salt thereof wherein

Ar is phenyl, 1- or 2-naphthyl, 2-, 3-, or 4-pyridinyl, or 4- or 5-pyrimidinyl, each of which is mono-, di-, or trisubstituted with halogen, hydroxy, $C_1$–$C_6$ alkyl, or $C_1$–$C_6$ alkoxy with the proviso that at least one of the positions on Ar ortho to the point of attachment to the isoquinolinamine ring is substituted;

$R_3$ and $R_4$ are the same or different and represent
hydrogen, $C_1$–$C_6$ alkyl optionally substituted with halogen, hydroxy, or $C_1$–$C_6$ alkoxy; or
aryl ($C_1$–$C_6$)alkyl, where aryl is phenyl, 1- or 2-naphthyl, 2-, 3-, or 4-pyridinyl, 2- or 3-thienyl or 2-, 4-, or 5-pyrimidinyl, each of which is optionally mono- or disubstituted with halogen, hydroxy, $C_1$–$C_6$ alkyl, $C_1$–$C_6$ alkoxy; or $C_1$–$C_6$ alkyl-Y—$R_5$, wherein Y is O, S, NH, or N($C_1$–$C_6$ alkyl), and $R_5$ is hydrogen or $C_1$–$C_6$ alkyl; and $R_6$ is hydrogen or $C_1$–$C_6$ alkyl.

14. A compound according to claim 13, wherein Ar is phenyl trisubstituted in the 2, 4, and 6 positions relative to the point of attachment to the isoquinolinamine ring with $C_1$–$C_2$ alkyl.

15. A compound according to claim 14, wherein Ar is 2,4,6-trimethylphenyl and at least one of $R_3$ or $R_4$ is $C_1$–$C_6$ alkyl or phenyl (C$_1$–C$_6$)alkyl wherein the phenyl group is unsubstituted or substituted with (C$_1$–C$_4$)alkyl or halogen.

16. A compound according to claim 1, which is N-Cyclopropylmethyl-N-propyl-4-(2,4,6-trimethylphenyl)-1-phthalazinamine.

17. A compound according to claim 1, which is N-Cyclopropylmethyl-N-ethyl-4-(2,4,6-trimethyphenyl)-1-phthalazinamine.

18. A compound according to claim 1, which is N-Cyclopropylmethyl-N-methyl-4-(2,4,6-trimethyphenyl)-1-phthalazinamine.

19. A compound according to claim 1, which is N-Cyclopropylmethyl-N-(2-methoxyethyl)-4-(2,4,6-trimethyphenyl)-1-phthalazinamine.

20. A compound according to claim 1, which is N-Benzyl-N-ethyl-4-(2,4,6-trimethyphenyl)-1-phthalazinamine.

21. A compound according to claim 1, which is N-(2'-Chlorophenylmethyl-N-ethyl-4-(2,4,6-trimethyphenyl)-1-phthalazinamine.

22. A compound according to claim 1, which is N-(4'-Chlorophenylmethyl-N-ethyl-4-(2,4,6-trimethyphenyl)-1-phthalazinamine.

23. A compound according to claim 1, which is N-(2'-Tolymethyl)-N-ethyl-4-(2,4,6-trimethyphenyl)-1-phthalazinamine.

24. A compound according to claim 1, which is N-(2'-Methoxyphenylmethyl)-N-ethyl-4-(2,4,6-trimethyphenyl)-1-phthalazinamine.

25. A compound according to claim 1, which is N-(2'-Pyridylmethyl)-N-ethyl-4-(2,4,6-trimethyphenyl)-1-phthalazinamine.

26. A compound according to claim 1, wherein R$_3$ and R$_4$ are not hydrogen simultaneously and W is N or CH.

27. A compound according to claim 6, wherein R$_3$ and R$_4$ are not hydrogen simultaneously.

28. A compound according to claim 9, wherein R$_3$ and R$_4$ are not hydrogen simultaneously and W is N or CH.

29. A compound according to claim 13, wherein R$_1$ and R$_2$ are not hydrogen simultaneously and W is N or CH.

* * * * *